(12) United States Patent
Isoda et al.

(10) Patent No.: US 6,740,521 B2
(45) Date of Patent: May 25, 2004

(54) HIGH-SENSITIVE DETECTION OF ENVIRONMENTAL POLLUTANTS

(75) Inventors: Hiroko Isoda, Tsukuba (JP); Takashi Koyama, Yuki (JP); Masako Tasaki, Tsukuba (JP); Syuichi Oka, Tsukuba (JP); Norio Sugiura, Tsuchiura (JP); Takaaki Maekawa, Ibaraki (JP); Yuhei Inamori, Tsukuba (JP); Shinichi Yokota, Takasago (JP); Mikio Kitahara, Kobe (JP); Kazuhiro Nagata, Kyoto (JP)

(73) Assignees: Kaneka Corporation, Osaka (JP); Agency of Industrial Science and Technology, Tokyo (JP); Ministry of International Trade and Industry, Tokyo (JP)

( * ) Notice: Subject to any disclaimer, the term of this patent is extended or adjusted under 35 U.S.C. 154(b) by 0 days.

(21) Appl. No.: 10/094,151

(22) Filed: Mar. 11, 2002

(65) Prior Publication Data

US 2003/0049737 A1 Mar. 13, 2003

(30) Foreign Application Priority Data

Sep. 7, 2001 (JP) ......................................... 2001-272478

(51) Int. Cl.⁷ .......................... C12N 5/00; C12N 15/00; C12P 21/06; C12Q 1/68; C07H 21/04
(52) U.S. Cl. ..................... 435/325; 435/69.1; 435/91.1; 435/320.1; 435/6; 536/24.1; 514/2; 514/44
(58) Field of Search .......................... 435/6, 69.1, 91.1, 435/320.1, 325; 534/24.1; 514/321, 422

(56) References Cited

U.S. PATENT DOCUMENTS 6,117,643 A * 9/2000 Simpson et al. ............. 435/7.1
6,281,229 B1 * 8/2001 Yokota et al. ............... 514/321

FOREIGN PATENT DOCUMENTS

| JP | 10-108678 | 4/1998 |
| WO | WO 90/02947 | 3/1990 |
| WO | WO 94/17208 | 4/1994 |
| WO | WO 99/16903 | 4/1999 |
| WO | WO 01/42423 A2 | 6/2001 |

OTHER PUBLICATIONS

I Herr and K Debatin, "Cellular stress response and apoptosis in cancer therapy". Blood 98(9), pp. 2603–2614).*
N. Hosokawa et al., "Structure of the Gene Encoding the Mouse 47–kDa Heat–shock Protein," Gene (1993) 126:187–193, Elsevier Science Publishers B.V.
T. K. Van Dyk et al., "Rapid and Sensitive Pollutant Detection by Induction of Heat Shock Gene–Bioluminescence Gene Fusions," *Applied and Environmental Microbiology* (May 1994) 60(5):1414–1420, ©American Society for Microbiology.

* cited by examiner

*Primary Examiner*—Remy Yucel
*Assistant Examiner*—Maria Marvich
(74) *Attorney, Agent, or Firm*—Foley & Lardner

(57) ABSTRACT

The present invention provides a bioassay system, for detection of hazardous chemical substances, natural toxic substances in the environment and unknown toxic compounds, with high sensitivity, simplicity and speed. The invention provides cells and a method of using the cells for use in the bioassay system. The cell provided by the invention contains a heat shock factor binding DNA sequence and a transcriptional regulatory sequence necessary on an occasion of stress induction as a transcriptional regulatory factor binding site. The cell also possesses a reporter gene under the control of the promoter. The reporter gene is connected, on the downstream side, to the SV40pA signal without any intervening intron.

12 Claims, 7 Drawing Sheets

* pGlacpA471 is 6.3 kb in size, and pGlacIntpA471 is 7.1 kb in size.

HIGH-SENSITIVE DETECTION OF ENVIRONMENTAL POLLUTANTS

CROSS-REFERENCE TO RELATED PATENT APPLICATIONS

Japan Priority Application 2001-272478, filed Sep. 7, 2001 including the specification, drawings, claims and abstract, is incorporated herein by reference in its entirety.

FIELD OF THE INVENTION

This invention relates to highly sensitive cells that can detect environmental pollutants as well as to the detection methods employed.

BACKGROUND OF THE INVENTION

Currently, evaluation of the toxicity of environmental pollutants is accomplished by instrumental analysis or bioassays using test organisms. Instrumental analysis using, for example, HPLC, GC/MS or LC/MS, enables highly sensitive detection of environmental pollutants and these techniques have been established as a means for analyzing specific known components. Bioassays using mammalian, microbial and fish test organisms precisely reflect the effects of chemical substances on living organisms. However it is substantially impossible to test the effect of large numbers chemicals individually, without taking into account any synergistic effects multiple chemicals may have when tested together because these tests require a large number of animals. The difficulty is compounded when examining the effects of long-term exposure and effects over multiple generations. Thus, simple and economical methods of testing the effect of chemicals on a biological system are needed.

At present, some in vitro assay systems are known. Compounds are tested for mutagenicity using detection systems such as the Ames test, chromosomal aberration tests which uses cultured cells and the cytotoxicity test which measures cell growth rates. Additionally, new detection systems can detect characteristic features like estrogenic response using human breast cancer cells MCF-7 cells that express estrogen receptors. For example, vitellogenin, which usually appears in blood of female fish, is induced in male fish when they are exposed to xenoestrogen. Reporter assays are also known using cells transformed with a luciferase reporter gene.

Chemicals of social concern are not always detected by the conventional acute toxicity tests. Atmosphere, water and soil contain not only heavy metals but also various kinds of pollutants, including plastics, plasticizers, agrochemicals, plant estrogen etc., which are suspected endocrine disrupters. For example, heavy metals are known toxins and recent research reveals that some chemicals act as endocrine disrupters, but in many cases, the toxic mechanisms are unknown. It is possible our bodies are exposed to such chemicals, which are accumulated through food chains. Therefore, systems are demanded which can detect chemicals that cannot be evaluated by conventional methods or low exposure effects.

Another example is the occurrence of water blooms of phytoplankton are found in both fresh water and marine environment. Cyanobacteria blooms occur in water containing adequate levels of essential inorganic nutrients such as nitrogen and phosphorus. Some species of cyanobacteria produce toxins which are classified according to their mode of action into hepatotoxins (e.g. microcyctins, nodularins), neurotoxins (e.g. anatoxins), skin irritants and other toxins. Toxic water blooms have caused death in domestic and wild animals as well as human illness. Recently, it was reported that dialysis patients in Brazil died of acute hepatic failure due to cyanobacteria contamination of the water used. These toxins are not only present in the water, but are also accumulated in shellfish such as shrimps, prawns and lobsters. Therefore, such toxins may damage human health.

Methods of detecting microcystins are known. LC/MS provides a means of highly sensitive analysis of known individual components in a sample. It is also possible to detect microcystins using an enzyme immunoassay. Additionally, a simpler method of detecting the presence of microcystins exploits the, specific inhibitory activity of microsystins in protein phosphatase 1 and 2 activity assays in enzyme activity assays Acute toxicities can be studied by their effect on functional disorders in animals or cultured cells. However, it requires much time and cost to obtain results with utmost confidence. Many kinds of chemicals are found in low concentrations in most environments so that it is difficult to detect these substances rapidly.

Therefore a rapid and simple assay, which enables the evaluation of effects on human and on ecosystems by endocrine disrupters and heavy metals is required. Environmental pollution has become more complicated, synergistic and long-term effects are now a serious problem. This discussion demonstrates the importance of bioassays and indicates the risk and use for the assessment.

In Chemical Abstracts, a database of chemical substances, about twenty million of substances have been registered. In Japan, about sixty thousand chemical substances are in daily use and, reportedly, not less than about ten thousand synthetic chemical substances have been or are being accumulated in the environment. Hazardous chemical substances, typically endocrine disrupters, whose toxicity can hardly be predicted by conventional toxicological methods are now known. Thus, it has become important to correctly understand the hazardous features possibly caused by those substances in order to facilitate protective measures or countermeasures.

Instrumental analysis by GC/MS or LC/MS technique can separate, identify and quantify single individual components, but are not suited as means to totally analyze or evaluate the influences of multiple components on living organisms. It is anticipated that a vast sum of time and cost will be required to individually investigate the influences of these known or unknown chemical substances occurring in trace amounts in humans or in the environment by these conventional instrumental methods. There is also a possibility that a plurality of chemical substances, each occurring in trace amounts, may produce a synergistically increased or modified influence on humans and environment. In particular, the landfill leachate of industrial wastes or the byproduct of refuse incineration contains not only known existing hazardous substances, but also unknown chemical substances. It is very difficult to investigate the hazardous features of such compounds individually, to say nothing of detecting synergistically enhanced complex contamination by a plurality of substances. Currently, however, such hazardous substances have been revealed as occurring in the environment one after another and, therefore, a method of rapidly detecting, with high sensitivity, the risk of hazardous chemical substances, including unknown chemical substances, occurring in the environment, is required.

In addition to in vivo methods using fish or mammals, are biological methods of evaluating the impact of hazardous chemical substances. Such in vitro methods, using cultured microbial or animal cells, can detect the binding of a hazardous chemical substance to a specific target protein. In some of these biological methods (bioassays), the influence of a test substance is detected by utilizing the specific response of the cell type used or of the derived tissues to the substance. In those cases, it is assumed that microorganisms, including yeasts, plants, fish and animal cells will react to the chemical substance. Furthermore, even in those systems in which human cells are used, the conventional bioassays detect the effect of trace chemical substances on cells via binding to a cell-specific receptor or receptors and as such are unable to generate complete information rapidly and with high accuracy.

In this respect, it is known that the stress response system, in particular the heat shock protein (HSP) inducing system, functions in all mammalian tissues and cells. Therefore, in bioassay systems utilizing this stress response, it is not necessary to take into consideration the basic problems regarding cell specificity. Furthermore, in the actual environment, e.g. in landfill leachate, although many pollutants are present this may only account for a few percent of total organic carbon as determined by GC/MS. Therefore, leachate possibly includes numerous unknown hazardous chemicals. In the art, there are many compounds whose toxicities are unknown, thus making it difficult to make an accurate list as well as to evaluate their hazardous effects. There has been no easily implemented, trustworthy system for accomplishing the above object using the HSP promoter. A system for quantitative detection of the common response of various cells to toxic factors and for maintenance of homeostasis in living organisms, that is to say the response to stresses, is needed. This system should prove to be a highly sensitive detection system for hazardous environmental pollutions, thus providing solutions to the above problems.

Since microcystins have a difference in toxicity between homologs, a simple evaluating system for low concentration microcystins is desired. *J. Chem. Soc. Perkin Trans.* 1:2311, (1984) It has reported that these biotoxins not only have acute toxicity but also serve as promoters of carcinogenesis, *J. Cancer Res. Clin. Oncol* 180:420(1992). However the exact mechanism of toxicity is not clearly understood. Because all natural toxic substances, including modifications of those substances, have not been identified, bioassays for detecting toxicity of an unidentified toxic substance, including analogs, or toxicity due to the presence of a plurality of natural toxic substances in low concentrations is required. This bioassay should reflect physiological conditions as much as possible and should be able to be performed rapidly. Thus, a highly sensitive total detection and evaluation assay is desired.

If the general response of various cells to toxicity or stress can be detected quantitatively in a certain system, this will be expected to be an effective method that can clear many problems for total detection of biotoxins, including microcystin.

SUMMARY OF THE INVENTION

The present invention relates to a highly sensitive system for detecting trace amounts of environmental pollutants and natural toxins. Cells were transformed with a heat shock factor binding site connected to a reporter gene to obtain a stable cell line. To assay the reporter protein, which is induced by activation of the former heat shock factor sequence, the effects of the hazardous chemicals can be quantitatively evaluated.

Thus, in a first aspect, the present invention provides a cell which is obtained by transfer of a promoter containing a heat shock factor binding DNA sequence and a transcriptional regulatory sequence necessary on an occasion of stress induction as a transcriptional regulatory factor binding site, as well as a reporter gene under the control of the above-mentioned promoter into a chromosome, said reporter gene being connected, on the downstream side thereof, to the SV40pA signal without any intron, and which is used for detecting chemicals or natural toxins which disrupt or disturb homeostasis of organisms, by measuring said reporter gene protein inducing activity.

The "cell which is obtained by transfer of the gene into a chromosome" refers to as a stable transformant as distinguished from a cell in a transient expression system.

As the heat shock factor binding DNA sequence, includes, for example, the heat shock factor binding sequence occurring in the human HSP promoter, the mouse HSP promoter, and the Drosophila HSP promoter.

The "transcriptional regulatory sequence necessary on an occasion of stress induction" refers to a transcriptional regulatory sequence which functions on the occasion of stress induction of a protein but not transcriptional regulatory sequence which functions independently of stress induction (specifically the AP-1 binding DNA sequence or the NF-B binding DNA sequence). Preferably, the cell of the present invention does not contain any transcriptional regulatory sequence which functions independently of stress induction. Specific examples of the transcriptional regulatory sequence necessary on the occasion of stress in-duction, include the SP1 factor binding DNA sequence and GAGA factor binding DNA sequence, which are necessary for immediate response of the promoter when the cell is placed under stress.

The promoter containing a heat shock factor binding DNA sequence and a transcriptional regulatory sequence necessary on an occasion of stress induction as a transcriptional regulatory factor binding site is not particularly restricted provided that is has the above two DNA sequences. Examples of suitable promoters include the heat shock gene promoter, HSP47 promoter and HSP100 promoter. The heat shock gene promoter is preferred. Also preferred is the HSP47 promoter containing the heat shock factor binding DNA sequence and SP1 factor binding DNA sequence.

The reporter gene is preferably one that provides for easy and rapid enzyme assay. Examples of suitable reporter genes include the β-galactosidase gene and the genes coding for such proteins as luciferase, chloramphenicol acetyltransferase and alkaline phosphatase.

In the above cell, the SV40pA signal (*Mol. Cell. Biol.* 10:4248, (1989)) is preferably connected to the above reporter gene on the downstream side thereof. In this case, it is more preferred that no intron be introduced immediately before the SV40pA signal.

The above cell is preferably constructed from a cultured animal cell. The above cell is preferably a stable transformant derived from a Chinese hamster ovary (CHO) cell or HeLaS3 cell. The mentioned cell is preferably CHO-derived stable transformant 2F1813. (This cell strain was deposited on Aug. 17, 2001 at National Institute of Advanced Industrial Science and Technology International Patent Organism Depositary and given a domestic deposition number, FERM P-18473. It was transferred to the international deposition phase based on the Budapest Treaty and on Feb. 7, 2002, given an international deposition number, FERM BP-7876).

In a second aspect, the present invention provides a method for detecting a hazardous chemical substance and/or a natural toxic substance disrupting or disturbing homeostasis in living organisms, which comprises culturing the above cell on a test sample containing medium and then measuring a reporter gene protein inducing activity.

This method can be applied in a method of evaluating a test sample containing an endocrine disrupter, a method of evaluating a test sample obtained from the environment and containing environmental standard substances, a method of evaluating a test sample containing a heavy metal, and a method of evaluating a test sample containing two or more different hazardous chemical substances in admixture, inclusive of an unidentified substance.

Preferably, the natural toxic substance is a toxin produced by blue-green algae. More preferably the natural toxic substances are microcystins or nodularins.

In a third aspect, the present invention provides a kit for detecting a hazardous chemical substance or a natural toxic substance disrupting or disturbing homeostasis in living organisms, which comprises the above cell.

In the above kit, there may be contained reagents necessary for detecting a hazardous chemical substance or a natural toxic substance disrupting or disturbing homeostasis in living organisms, for example, a medium, a solvent in which a test sample may be dissolved and a substrate which can measure a reporter gene protein inducing activity, and so forth.

DETAILED DESCRIPTION OF THE PREFERRED EMBODIMENTS

Figure 1:
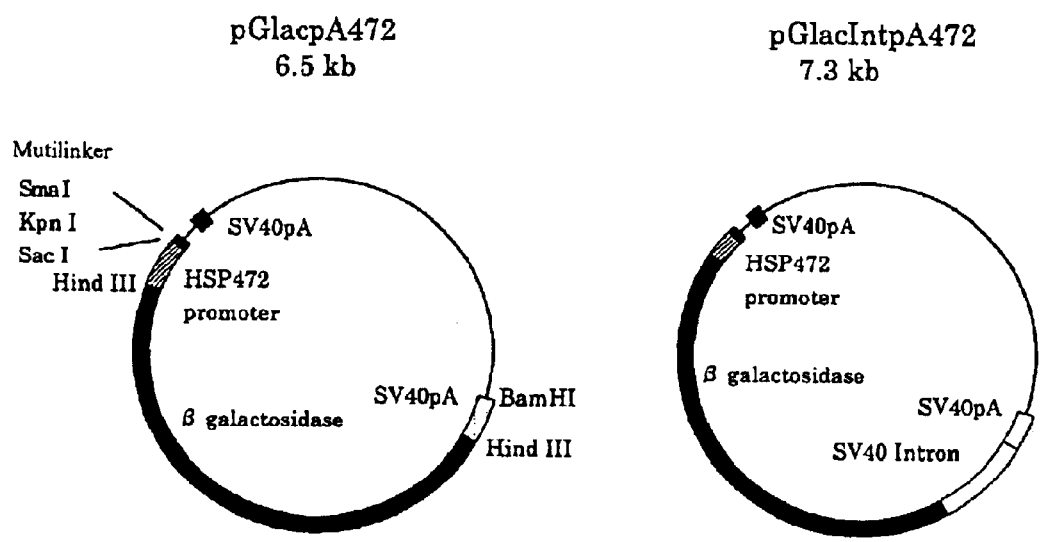
FIG. 1 is a schematic representation of the structures of expression plasmids and HSP47 promoters.
Figure 1:
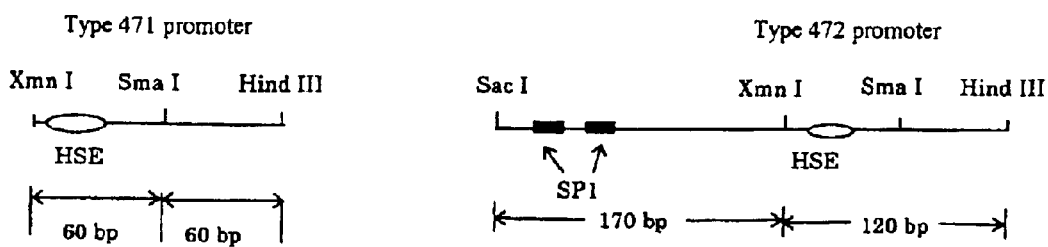

Plasmids used in producing the cell of the invention can be, for example, a plasmid derived from the HSP47 promoter sequence (*Gene* 126:187, 1993) having the SP1 (specificity protein 1) factor binding DNA sequence (*Cell* 72:247, 1993) and heat shock factor (HSF) binding DNA sequence (*Mol. Cell. Biol.*, 8:3761, 1987) and having none of the AP-1 binding DNA sequence (*Proc. Natl. Acad. Sci. USA* 88:3720, 1991) or the NF-B binding DNA sequence (*Biochem. Biophys. Acta* 1072:63, 1991) is connected with, on the downstream side of the promoter, the β-galactosidase gene and further connected with, on the downstream side thereof, the SV40pA signal without any intron. When introduced into a chromosome, this plasmid can express β-galactosidase efficiently by stress induction.

The heat shock factor (HSF) binding DNA sequence means an inverted repeat structure having the DNA sequence 5'nGAAn3' (n being an arbitrary DNA base) as one unit. An example is the sequence 5'nGAAnnTTCn3' and, as a result of analysis of the heat shock protein gene, it has been revealed that the occurrence of two or more successive 5'nGAAn3' units in the inverted repeat structure are necessary for stress response. It is also estimated that three or more are required for satisfactory functioning in the chromosome. In the HSP47 promoter, there are three successive 5'nGAAn3' units as inverted repeats.

The SP1 factor binding DNA sequence is a DNA sequence on the promoter and called the GC box. It is considered to be a DNA methylation regulatory site occurring in the SV40 early promoter or HSP47 promoter. Recently, in particular, studies have been made concerning DNA methylation from the chromosomal gene expression regulation viewpoint.

When bound to a GA repeat sequence of a DNA, the GAGA factor destructs the regular nucleosome structure of a chromosome, facilitating binding of the the transcription factor binding to the promoter (*Mol. Cell. Biol.* 13:2802, 1993).

AP-1 is a gene regulatory protein having a heterodimeric structure composed of the Jun protein and Fos protein, and NF-B is a gene regulatory protein having a heterodimeric structure composed of the p50 and p65 proteins.

The reporter gene expressing the reporter protein is preferably one enabling simple and rapid enzyme assay. Suitable reporter genes include, for example the β-galactosidase gene and, in addition, the genes encoding such proteins as luciferase, chloramphenicol acetyltransferase and alkaline phosphatase. The reporter gene DNA can be obtained, for example, by restriction enzyme digestion of a commercially available plasmid DNA. The plasmid mentioned above can be constructed by the conventional genetic engineering techniques described in, for example Sambrook et al. MOLECULAR CLONING, 2nd edition, Cold Spring Harbor Laboratory Press (1989).

Cells suitable for construction of the stable transformant of the present invention include, for example, cells derived from mammals such as Chinese hamster, human, mouse and rat. More specific examples are CHO cell-derived CHO-K1 cells and HeLaS3 cells which can be obtained from the American Type Culture Collection (ATCC). In an embodiment of the present invention, the cell of the invention can be obtained by transforming an animal cell, such as a CHO-K1 cell, with the above plasmid by, for example, the calcium phosphate method or electroporation technique. The cell to be transformed need not be only a CHO-K1 cell but also any of those cultured animal cells which can be stably subcultured.

Experiments made by the present inventors revealed that even when there is no SP1 factor binding DNA sequence in the promoter of the plasmid to be used for transformation, stress induction is possible and that, in particular when the transient expression of a reporter gene is measured, a plasmid containing no SP1 factor binding DNA sequence causes stronger stress induction as compared with a plasmid containing the SP1 factor binding DNA sequence. Specifically, in the case of transient expression in CHO-K1 cells, the pGlacpA471 vector having the mouse HSP47 promoter (the type 471 promoter in FIG. 1) containing no SP1 factor binding DNA sequence, when heat-treated, showed a reporter protein activity about three times higher than that found without heat treatment whereas the pGlacpA472 vector having the mouse HSP47 promoter (the type 472 promoter in FIG. 1) containing the SP1 factor binding DNA sequence, when heat-treated, showed a fluorescence intensity only about 1.7 times higher than that found without heat treatment.

Figure 2:
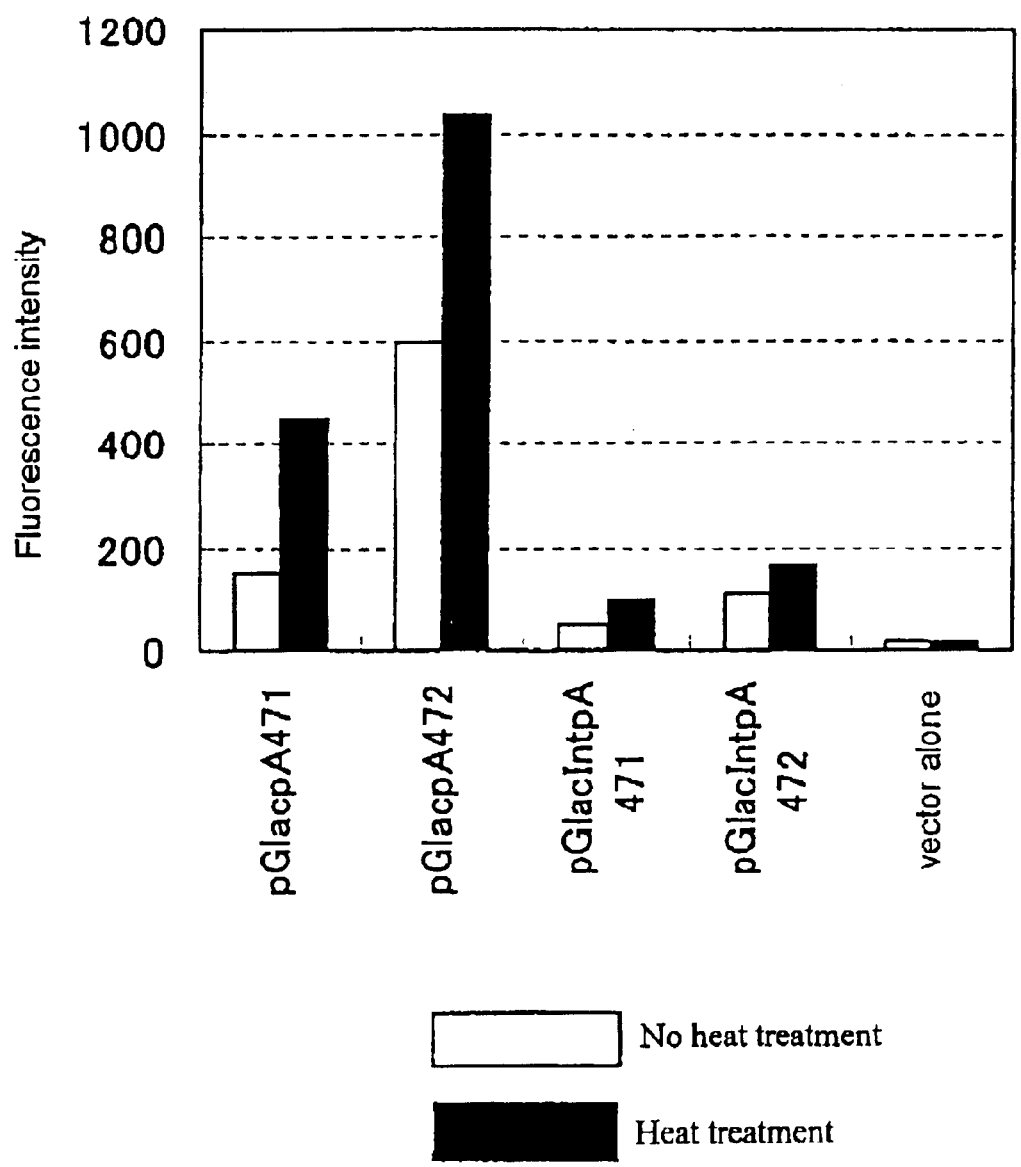
FIG. 2 is a graphic representation of the comparison of β-galactosidase transient expression activity on heat treatment in CHO-K1 cells transformed with the expression plasmids.
Figure 3:
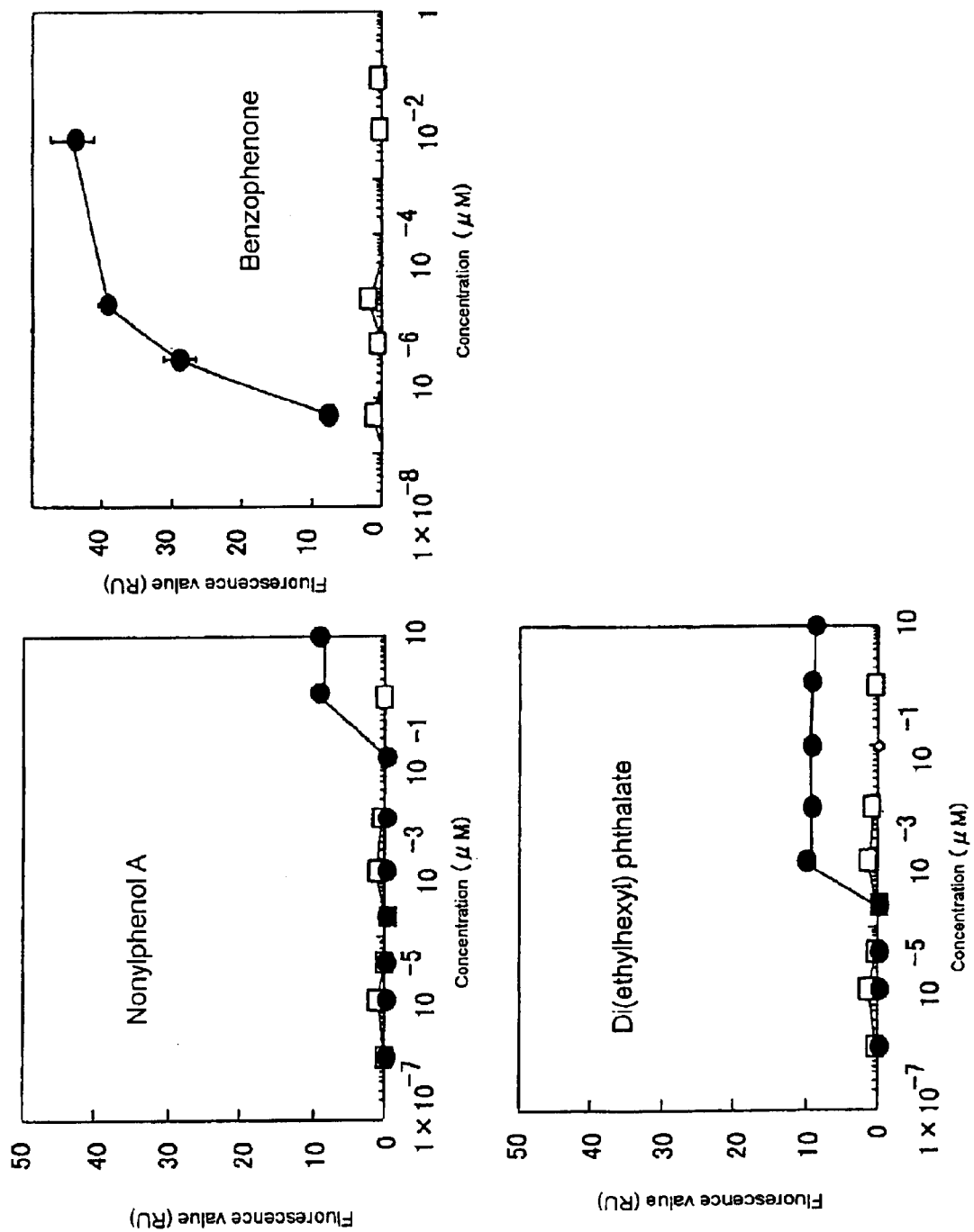
FIG. 3 is a graphic representation of the relationship between the test substance concentration and β-galactosidase inducing activity in 2F1813 cells and 5K95 cells treated with the various hazardous chemical substances.
Figure 4:
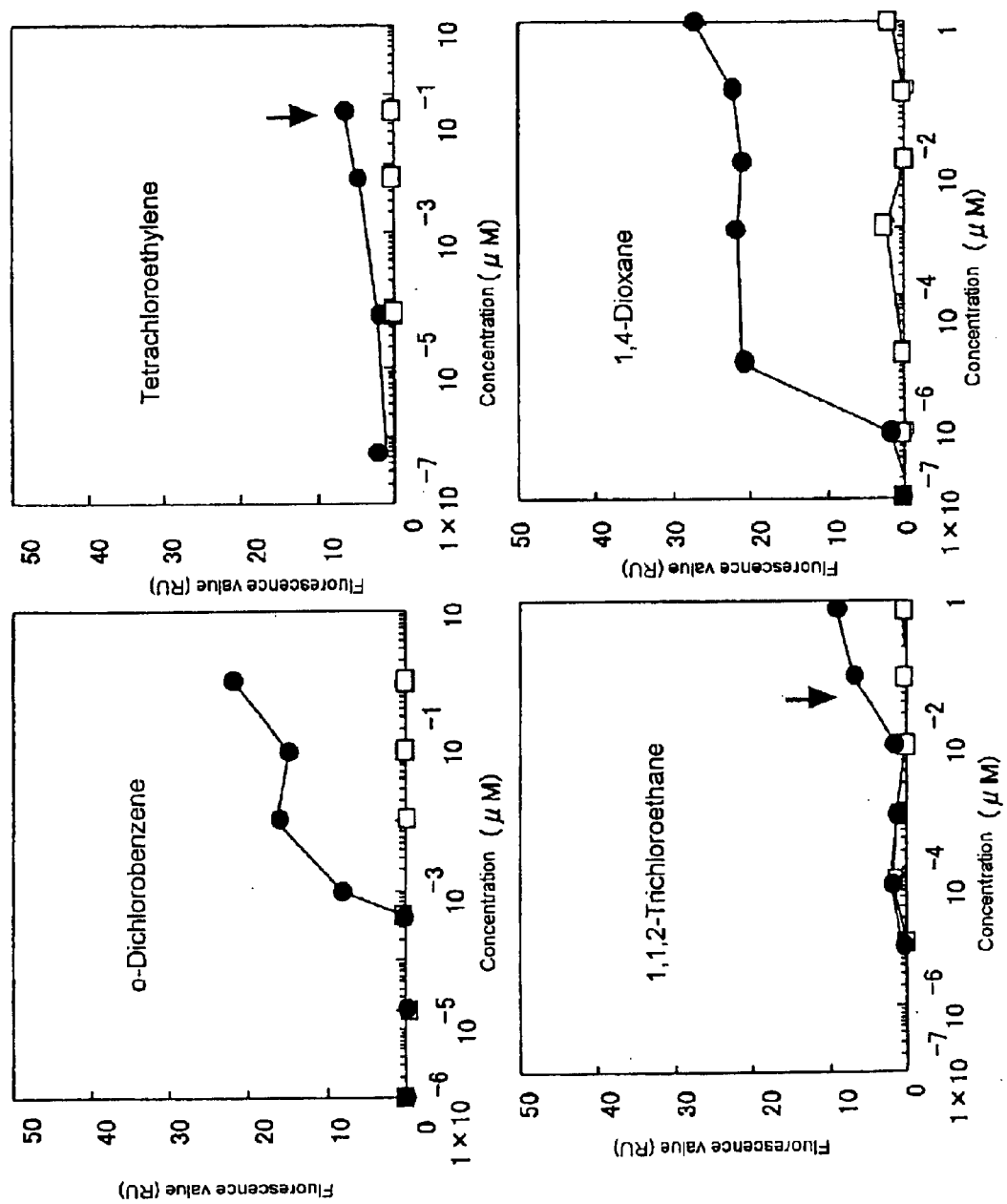
FIG. 4 is a graphic representation of the relationship between the test substance concentration and β-galactosidase inducing activity in 2F1813 cells and 5K95 cells treated with the various hazardous chemical substances.
Figure 5:
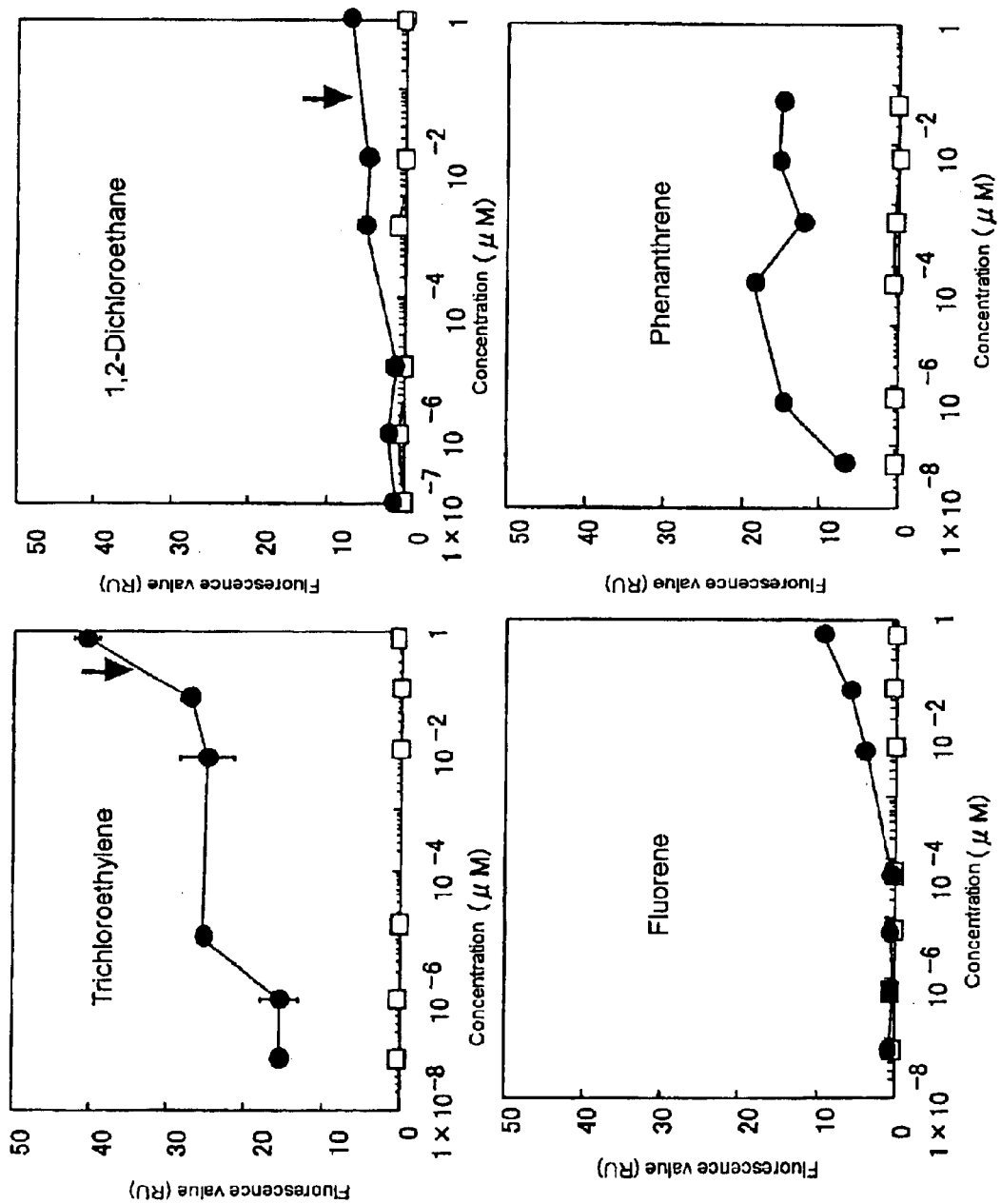
FIG. 5 is a graphic representation of the relationship between the test substance concentration and β-galactosidase inducing activity in 2F1813 cells and 5K95 cells treated with the various hazardous chemical substances.
Figure 6:
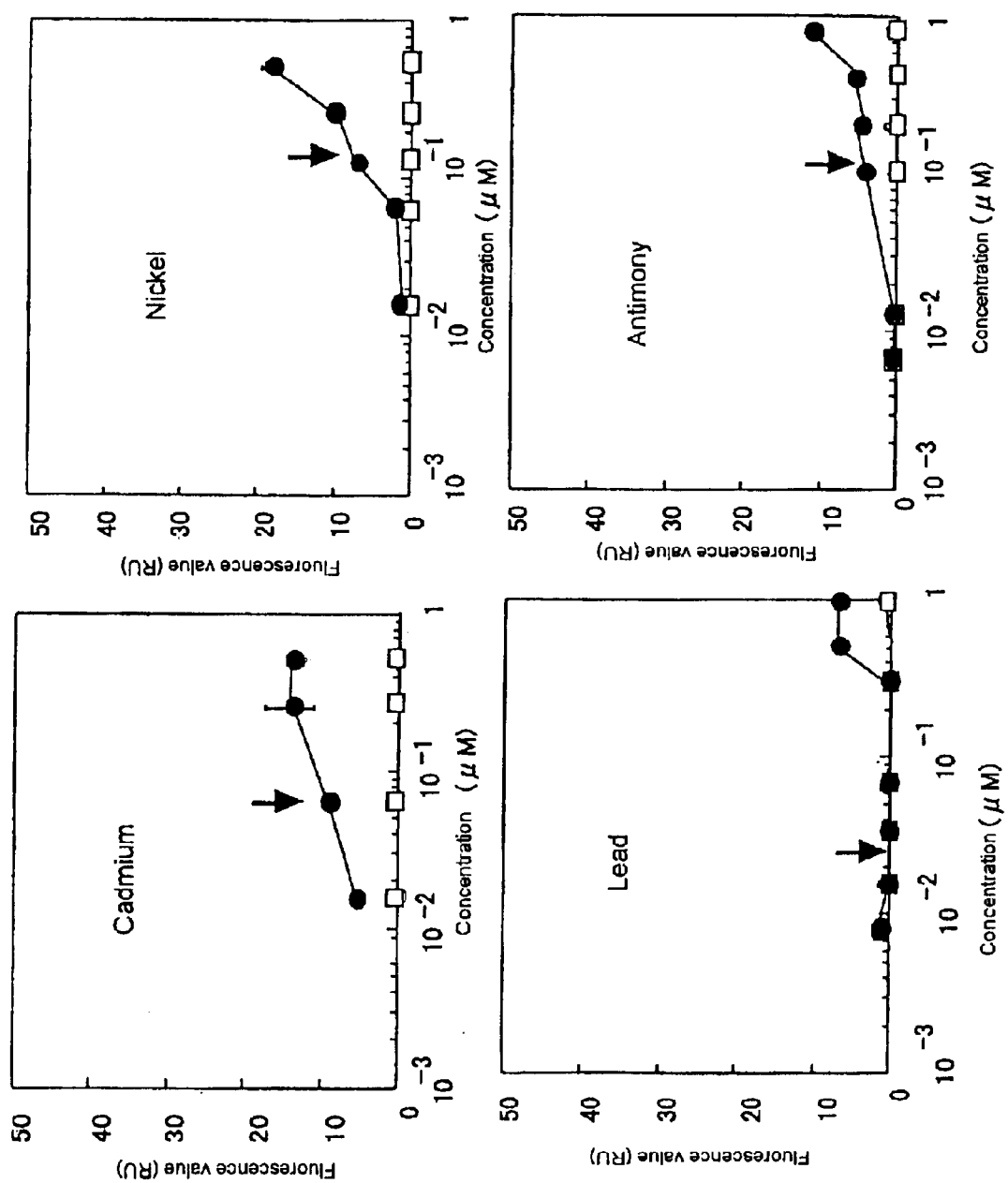
FIG. 6 is a graphic representation of the relationship between the test substance concentration and β-galactosidase inducing activity in 2F1813 cells and 5K95 cells treated with the various hazardous chemical substances.

Experiments made by the present inventors also revealed that expression plasmids having no intron immediately before the SV40pA signal cause stress induction of a reporter protein about 4 times higher than the conventional expression plasmids having an intron immediately before the SV40pA signal (FIG. 2).

In the case of transient expression, however, it was found that a considerable expression of a reporter protein is observed as a background in no-stress treated control groups and that when the stressor stimulation is weak, the sensitivity decreases. This decrease in sensitivity is disadvantageous in measuring hazardous chemical substances occurring in trace amounts in the environment. The inventors found that this problem can be solved by obtaining stable transformants of cultured animal cells using the above plasmid. This solution has been reached only after experimentation using not only the HSP47 promoter but also the SP1 factor binding DNA sequence, SV40pA signal and intron.

It is a matter of course that animal cells transformed with the same plasmid markedly differ in stability and inductivity according to the site of integration in chromosome and other factors. The best mode of embodiment is the Chinese hamster ovary cell-derived stable transformant 2F1813 (this was deposited on Aug. 17, 2001 at National Institute of Advanced Industrial Science and Technology International Patent Organism Depositary and given a domestic deposition number, FERM P-18473. It was transferred to the international deposition phase based under the Budapest Treaty and on Feb. 7, 2002, given an international deposition number, FERM BP-7876). The most convenient cell strain can be selected by carrying out multiple cell screenings to determine stress responsiveness, gene stability, etc. The desired transformants can be easily acquired by effecting simultaneous transformation with a drug resistance gene, such as the neomycin resistance gene. The drug resistance gene should be in the form of a plasmid in which it is constitutively expressed and this plasmid must be effective in animal cells. It is also possible to integrate a suitable drug resistance gene in the above-mentioned plasmid where the gene is constitutively expressed.

It has now been found that stable transformants obtained by transformation with the above plasmid, in a stress-free condition, show reporter protein expression levels dramatically reduced as compared with the transient expression results. Thus, when the expression levels are compared between stress-free condition and under-stress condition, transient expression cells show an induction rate of at most 2 to 4 times that in stress-free condition, whereas stable transformants show scores of times higher induction rates. The above plasmid containing the SP1 factor binding DNA sequence and containing no intron immediately before the SV40pA signal, among others, gave stable transformants showing a very high level of stress induction, namely about 200 to 3,000 times or higher.

It is important, in evaluating the stress responses to chemical substances and so forth, to confirm that reporter protein expression by a control vector which is incapable of stress induction, for example the SV40 promoter, does not change significantly between the stress-free condition and under-stress condition. As a result of transformation of CHO-K1 cells with pGlacpA472, which is one of the embodiments of the above plasmid, and selection of stable transformants, a cell strain sharply responding to stress stimulation and inducing the expression of the β-galactosidase protein was obtained. This was named 2F1813 and deposited at National Institute of Advanced Industrial Science and Technology International Patent Organism Depositary on Aug. 17, 2001 (domestic deposition number FERM P-18473) and transferred to the international deposition phase on Feb. 7, 2002 (international deposition number FERM BP-7876).

It has already been revealed that the production of stress proteins is induced as a result of reaction of cells with a stressor such as heat, a chemical substance or a heavy metal. On the occasion of stress protein induction, a stress induced transcription factor, called heat shock factor, binds to the heat shock factor binding DNA sequence on the promoter DNA sequence, whereby synthesis of mRNA on downstream side thereof is started. When, utilizing this mechanism, a reporter gene connected to a stress-responding promoter is transferred into a chromosome and the relevant protein inducing activity is measured, it becomes less reactive to stimuli other than stress, whereby it becomes more effective.

The HSP47 promoter used in the present invention does not have various unnecessary regulatory factor binding DNA sequences other than the heat shock factor binding DNA sequence, which many other stress protein genes have. Of course, it is also possible to artificially construct a similar DNA sequence and use the same as a promoter for the above purpose. Further, as the vector to be used, there may be mentioned those plasmids suited for the genetic engineering in *Escherichia coli* and having an origin of replication and a drug resistance gene(s), each capable of functioning in microorganisms, as well as a number of restriction enzyme sites which can be utilized with ease.

In the art, there is a report about construction of a plasmid containing the chloramphenicol acetyltransferase gene connected to the mouse HSP47 promoter on the down-stream side thereof, transfer thereof into mouse BALB/3T3 cells and the subsequent transient expression in response to heat stress (Gene 126:187, 1993). However, the induced expression level is at most about 200 times in activity, and the variation thereof is large. The system of the present invention provides induction activity in response to heat of not less than 3,000 times, with little variation, and cells receive no stress stimulation due to transformation, so that the system is particularly accurate and reproducable making the present invention particularly suited for investigating the impact of low-concentration test substances.

There is another report concerning heat induction in a transient expression system using a plasmid containing the HSP70 promoter connected to the chloramphenicol acetyltransferase gene. However, the promoter region used in that study contains unnecessary transcriptional regulatory sequences such as the AP-1 binding DNA sequence, so that transcription is presumably under other influences such as growth as well as other signals. In this respect as well, the system according to the present invention is superior to the systems so far reported. There is no example known in the art of measuring a reporter protein that induces activity to thereby make it possible to detect low concentrations of hazardous chemical substances or natural toxic substances, namely microcystins, disrupting or disturbing homeostasis in living organisms.

By using the cell of the invention, it is possible to activate the heat shock factor gene transcription, namely to measure the toxicity of a test substance which is a stressor to the cell. For example, about $10^3$ to $5\times10^4$ cells according to the invention are seeded in each well of a 96-well plate. 100 to 200 µl/well of a medium containing a necessary amount of serum is added and the cells are cultured at 37° C. in the presence of 5% CO2 under saturated humidity conditions for 1 to 2 days. A test substance, either as it is or in a form dissolved in a solvent, is then added to fresh medium to give a test substance-containing medium. Suitable solvents are dimethyl sulfoxide (DMSO, ethanol, methanol and the like. After exchange of the medium for the test substance-containing medium, the cells are cultured for about one to several hours and, if necessary followed by further one to several hours of culture in a medium containing no test substance-free. Thereafter, the protein inducing activity of the reporter gene in the cells is measured quantitatively. When a solvent is used, a solvent control group is, of course, necessary.

Further, for distinguishing the heat shock factor activation, which is the main stress response, from the activation by other induction activation factors such as NF-B and AP-1, it is recommended that the DNA sequences to which those factors bind be not contained in the promoter. The plasmid mentioned above have no such DNA sequences that may cause backgrounds. Although cases are presumable where such other activation factors exert influences according to the site of integration in chromosome, such cases can be excluded by comparative experimental investigations in selecting stable transformants.

For further strictly detecting a stress-specific induction alone, a method is used which comprises detecting the induction of the reporter protein expression by the test substance using a control plasmid, which is a plasmid having no heat shock factor binding DNA sequence on the upstream side of the reporter gene but containing a promoter having a DNA sequence that binds another induction factor instead. For this purpose, it is possible to utilize the SV40 early promoter, for instance, which is a constant high level expression promoter.

Based on the fact that, in animal cells transformed with a stress responsive reporter gene, the reporter protein is induced by a test substance and, in animal cells transformed with a reporter gene under the control of the SV40 early promoter, the test substance does not cause any change in reporter protein expression, it is possible to detect contaminant substances or hazardous substances by measuring the stress-specific induction activity due to the test substance. That the reporter protein is induced in both transformants does not mean, as a matter of course, that the test substance is not hazardous.

A characteristic feature of the present invention is that those hazardous chemical substances which cannot be detected or can hardly be detected by the prior art bioassay systems can be detected rapidly with high sensitivity using the instant invention and further in that hazardous chemical substances changing in the environment with time can be detected without delay. Among the methods for the analysis of hazardous chemical substances, those systems which use experimental animals are thought to reflect the actual absorption, metabolism, accumulation and excretion systems. However, assays involving experimental animals are troublesome due to the time-consuming character of those assays as well as issues attendant with species specificity and. No methods have been established as yet for totally analyzing hazardous chemical substances occurring in the environment and, in particular, in a short time and in a simple and easy manner.

In an embodiment of the invention, it is possible to determine the toxicity of a test substance by adding the test substance to a culture of Chinese hamster ovary (CHO) cells transformed with the above plasmid, measuring the enzymatic activity of β-galactosidase and quantitatively evaluating the stress of the test substance upon the cells. When, however, the test substance shows nonspecific toxicity, the number of cells may decrease as a result of cell deaths or the reporter protein activity may apparently increase. In this case, the measurement and evaluation can be made by counting viable cells or by measuring the protein concentration in cells for relative comparison in terms of activity in total protein amount. On that occasion, it goes without saying that the method comprising determining the activity of a test substance by utilizing the reporter protein inducing activity of a stable transformant obtained by transformation with the above plasmid is particularly suited for evaluating test substances occurring in trace amounts, since the influences of the transformation procedure itself can be excluded as compared with the case of transient expression examination.

For detecting and evaluating hazardous chemical substances or natural toxic substances in the environment, the Chinese hamster ovary cell strain 2F1813 obtained by transfer of the β-galactosidase gene under the control of the HSP47 promoter and the Chinese hamster ovary cell strain 5K95 obtained by transfer of the β-galactosidase gene under the control of the SV40 promoter were used, and the β-galactosidase inducing activity was measured by adding the hazardous chemical substances or natural toxic substances in the environment to the system. On such occasion, cells seeded in advance on 96-well microplates 1 to 2 days prior to the test are incubated, after medium exchange with the test substance-containing media on the day of the test, at 37° C. for 1 to several hours in the presence of 5% $CO_2$. After removing the media, the cells are washed with two portions of PBS. 50 to 100 µl/well of a cell lysis solution (containing a surfactant such as NP-40; Promega's lysis buffer or the like may also be used) is added and the plates are allowed to stand for 20 to 120 minutes. After complete dissolution of cells by pipetting, each lysate is distributed in 10 to 20-µl portions into wells of a new 96-well plate. An additional 100 µl/well of a substrate solution (0.1 mM 4-methylumbelliferyl β-D-galactoside) is added, and the plate is covered with aluminum foil for shielding against light and allowed to stand at room temperature for 30 minutes. Thereafter, if necessary, an amount of 0.5 v/v of 1 M glycine-NaOH (pH 10.3) may be added as a reaction termination solution. Thereafter, the fluorescence values are measured at the excitation wavelength of 365 nm and the measurement wavelength of 450 nm using a fluorescence microplate reader.

Induction of the β-galactosidase activity expression was observed only in the 2F1813 stain with such endocrine disrupters as di(ethylhexyl)phthalate (DEHP) and nonylphenol, such environmental standard substances as o-dichlorobenzene and trichloroethane, and such heavy metals as cadmium and nickel, which all have been confirmed to be contained in landfill leachates whose influences on living organisms at low concentrations are matters of concern (FIG. 3 to FIG. 6). These results indicate that the system of the present invention is effective as a system for detecting hazardous chemical substances and the like.

Figure 7:
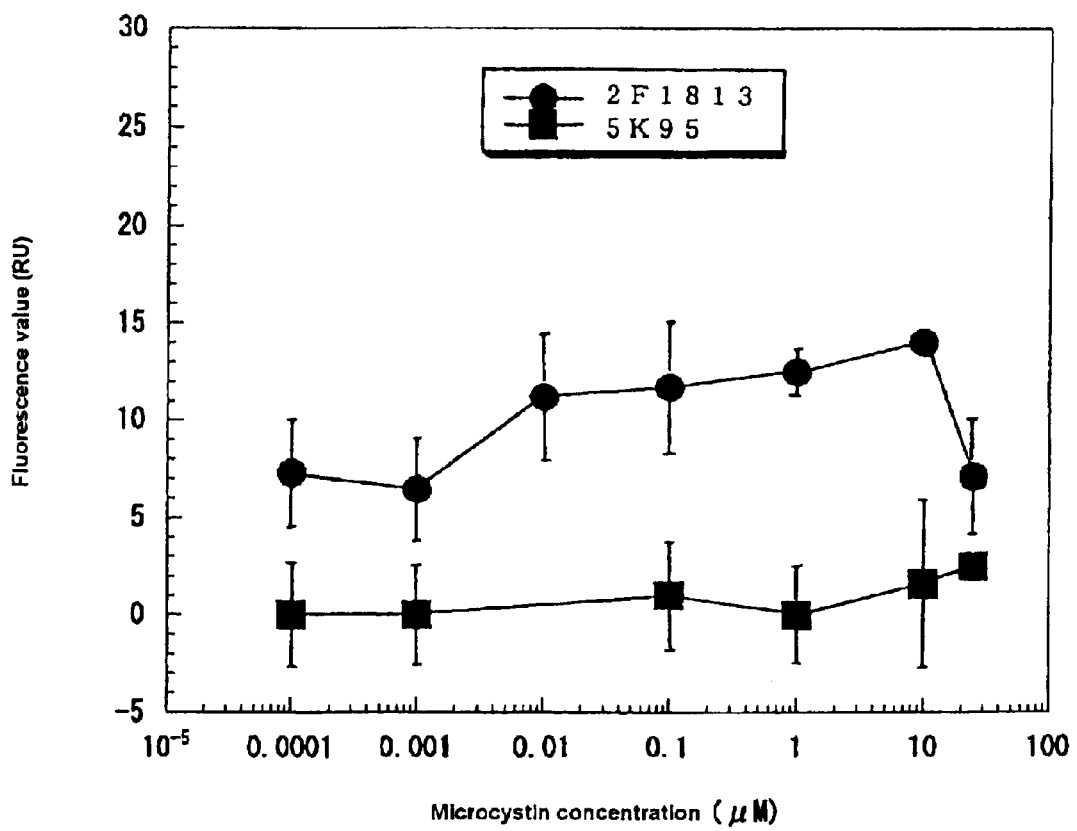
FIG. 7 is a graphic representation of the relationship between the test substance concentration and β-galactosidase inducing activity in 2F1813 cells and 5K95 cells treated with microcystin.

When the above cells were treated with microcystin for 3 hours, cells of the 2F1813 strain alone clearly showed an increase in β-galactosidase inducing activity (FIG. 7). When the microcystin treatment was conducted for 6 hours, the increase in β-galactosidase inducing activity tended to become weaker. These results indicate that the defense mechanisms in cells exposed to low concentrations of hazardous chemical substances or natural toxic substances can be detected with high sensitivity.

Microcystins are natural toxic substance produced by water blooms growing in lakes and marshes. They are hydrophobic substances with a molecular weight of about 1,000, composed of 5 amino acids common to the genus of microcystins and two L-amino acids. They are very stable against heat and hardly undergo proteolysis by trypsin and other proteases. At present, at least 60 homologs are known. Among them, microcystin LR is most toxic and comparable in toxicity to fugu poison (tetrodotoxin) or sarin, so that its influences, at low concentrations, on living organisms are currently matters of concern.

The detection system of the present invention which utilizes the 2F1813 strain is thus thought to be not only responsive to each individual substance but also effective as a means of evaluating aquatic environments where a variety of hazardous chemical substances occur in admixture since the induction of the reporter protein expression due to stress response can be observed even under situations where a plurality of compounds occur. As for the natural toxic substances, in lakes or marshes where the occurrence of microcystins, in particular, is suspected, low concentration contamination can be detected rapidly. Furthermore, even under situations where a plurality of compounds occur in admixture, the induction of the reporter protein expression due to stress response can be observed and, therefore, the detection system is thought to be effective as means of evaluating water environments where various hazardous chemical substances occur in admixture. In particular, the chemical influences thereof on the homeostasis in living organisms can be evaluated. Furthermore, it can be used also in evaluating those byproducts from dust incinerators and water treatment equipment or of landfill leachates of industrial wastes which contain an unidentified hazardous chemical substances.

The invention can provide a method for detecting the impacts or toxicities of various hazardous chemical substances or natural toxic substances in the environment or to homeostasis of living organisms and a method of evaluating such substances accordingly.

The following examples illustrate the present invention in further detail. These examples do not limit the scope of the present invention.

EXAMPLE 1

Construction of Vectors Capable of Inducing Expression of β-Galactosidase in a Stress-specific Manner The vectors shown in FIG. 1 were constructed. Thus, an expression plasmid named pGlacpA472 (6.5 kbp) was constructed by connecting the restriction enzyme AvaII (−197 to +38) fragment (cf. GENE, (126), 187, 1993) containing the heat shock factor binding DNA sequence (HSE) of the mouse HSP47 promoter to a 3.1-kb HindIII fragment containing the structural gene for β-galactosidase on the upstream side of the HindIII fragment in the direction enabling mRNA transcription, joining, immediately behind the same, about 220 bp from the restriction enzyme FbaI (nucleotide No. 2770 of SV40) site to the BamHI (nucleotide No. 2553) site of SV40 containing the SV40 late pA signal sequence, and connecting the resulting fragment to the BamHI-SacI fragment (about 3.2 kbp) containing the ampicillin resistance gene, of the pGL2 control vector (Promega) as the basic skeleton. pGlacpA471 (6.3 kbp) obtained by substituting the XmnI-HindIII fragment (about 120 bp), exclusive of the SP1 factor binding DNA sequence for the mouse HSP47 promoter region (about 290 bp) of pGlacpA472 was constructed in the same manner (cf. FIG. 1). Further, two expression vectors, pGlacIntpA472 (7.3 kbp) and pGlacIntpA471 (7.1 kbp), were constructed by inserting about 610 bp from the restriction enzyme MboI (nucleotide No. 4710 of SV40) site to the MboI site (nucleotide No. 4100) site of SV40 containing the SV40 intron, between the 3' terminus of the β-galactosidase gene and the SV40 late pA signal of pGlacpA472 and pGlacpA471, respectively (FIG. 1).

Stress-induced Reporter Protein Expression in Transformed CHO Cells (CHO-K1)

Dishes with a diameter of 6 cm were seeded with $2\times10^5$ Chinese hamster ovary cells (CHO-K1), which were then transformed with the plasmid of Example 1 by the conventional calcium phosphate method. The medium used was MD medium (MCDB 302: 5.5 g/liter, D-MEM: 4.75 g/liter, L-glutamine: 0.3 g/liter, NaHCO$_3$: 1.27 g/liter, kanamycin: 0.1 g/liter, pH 7.1) supplemented with a final concentration of 5% of FBS, and the culture was carried out at 37° C. in the presence of 5% CO$_2$.

After 2 days, cells were treated with heat (42° C.), a typical example of stress stimulation, for 90 minutes and, after further 2 hours of culture at 37° C., washed with two portions of PBS and added with 400 μl/dish of a cell lysis solution (Promega), and the mixture was allowed to stand at room temperature for 15 minutes and then distributed in 10-μl portions into wells of a 96-well white microplate. Thereto was added 100 μl/well of a substrate solution (0.1 mM 4-methylumberlliferyl β-D-galactoside solution prepared by diluting a stock substrate solution obtained by dissolving 4-methylumbelliferyl β-D-galactoside in dimethylformamide to a final concentration of 1% with a substrate diluting solution containing 10 mM sodium phosphate, pH 7.0, 100 mM NaCl, 1 mM MgCl$_2$, 0.1% BSA and 0.05% NaN$_3$), and the plate was then covered with aluminum foil for shielding against light and allowed to stand at room temperature for 30 minutes. Fluorescence values (RU) were measured at the excitation wavelength of 365 nm and the measurement wavelength of 450 nm using a fluorescent microplate reader for β-galactosidase activity detection. FIG. 2 shows the results of a comparison of β-galactosidase inducing activities transiently expressed in CHO-K1 cells transformed with the respective expression plasmids.

Stable transformants were obtained by selecting cell colonies grown on a medium supplemented with Geneticin (G418) to a final concentration of 200 μg/ml. Heat stress treatment was performed at 42° C. for 90 minutes, and cells were then cultured at 37° C. for 2 hours and subjected to β-galactosidase inducing activity detection according to the same procedure as mentioned above. Table 1 shows the results of a comparison of β-galactosidase inducing activities expressed upon heat treatment of stable transformants of CHO-K1 cells transferred with the respective expression plasmids.

TABLE 1

Fluorescence intensity (n = 3, mean value of RU)

| Vector | Transformant | Heat treatment | No heat treatment |
|---|---|---|---|
| pGlacpA471 | D | 42 | 13 |
|  | G | 78 | 8 |
|  | J | 47 | 10 |
|  | N | 70 | 8 |
| pGlacpA472 | B | 14 | 8 |
|  | F | 1418 | 10 |
|  | I | 792 | 4 |
|  | J | 51 | 8 |
|  | K | 59 | 8 |
|  | M | 413 | 3 |
|  | O | 55 | 8 |
| pGlacIntpA471 | C | 17 | 6 |
| pGlacIntpA472 | M | 270 | 5 |
| pSVβgal | A | 33 | 36 |
|  | D | 62 | 72 |
|  | G | 36 | 34 |
|  | I | 141 | 130 |
|  | L | 252 | 233 |
| None | CHO-K1 | 10 | 12 |

EXAMPLE 2

Preparation of CHO Cells for Detecting Environmental Contaminant Substances

Chinese hamster ovary (CHO) cells were transformed simultaneously with the plasmid pGlacpA472 having the β-galactosidase gene connected to the HSP47 promoter on the downstream side thereof and the neomycin resistance gene expression vector pSV2neo.Stable transformants were selected using the antibiotic G418. The stable transformants obtained were exposed to heat as a typical example of stress stimulation. The strain found to be most highly capable of inducing β-galactosidase activity expression was named 2F1813 (this was deposited on Aug. 17, 2001 at National Institute of Advanced Industrial Science and Technology International Patent Organism Depositary and given a domestic deposition number, FERM P-18473. It was transferred to the international deposition phase under the Budapest Treaty and on Feb. 7, 2002, given an international deposition number, FERM BP-7876) and used in the subsequent experiments.

For the purpose of preparing cells constituatively expressing the β-galactosidase protein irrespective of presence or absence of stimulation as a control, CHO cells were simultaneously transformed with a plasmid, pSV2βgalactosidase (Promega) having the β-galactosidase gene connected to the SV40 early promoter on the downstream side thereof and pSV2neo and then stable transformants were selected using the antibiotic G418. Among the stable transformants obtained, a cell strain highly and stably capable of expressing β-galactosidase was named 5K95 and submitted to the subsequent tests. Table 2 shows the results of a comparison of the β-galactosidase inducing activity of 2F1813 cells and that of 5K95 cells upon heat treatment or no heat treatment.

TABLE 2

|  | Heat treatment | No heat treatment |
|---|---|---|
| 2F1813 | 3305 | 1 |
| 5K95 | 630 | 813 |

Each value indicates the fluorescence intensity (RU).

EXAMPLE 3

Reporter Protein Activity Characteristics in Response to Environmental Pollution Culture of cells 2F1813 cells was used. The medium used was MD medium (MCDB 302: 5.5 g/liter, D-MEM: 4.75 g/liter, L-glutamine: 0.3 g/liter, NaHCO$_3$: 1.27 g/liter, kanamycin: 0.1 g/liter, pH 7.1) supplemented with a final concentration of 5% of FBS (fetal bovine serum) and 200 μg/ml of G418. Cells were cultured at 37° C. in 5% CO$_2$. Two days before the test, the wells of a 96-well plate were seeded with $1\times10^4$ cells/100 μl/well. The chemical substances tested were, di(ethylhexyl)phthalate (DEHP), benzophenone, nonylphenol A, o-dichlorobenzene tetrachloroethylene, 1,1,2-trichloroethane, 1,4-dioxane, trichloroethylene, 1,2-dichloroethane, fluorene and phenanthrene. These compounds were dissolved in methanol and then diluted at least 1,000-fold with MD medium after which they were used to treat the cells. Standard solutions (1,000 mg/l) of cadmium, nickel, lead and antimony (products of Nakalai Tesque) were diluted with the medium. The samples were then filtered using a 0.22 μm filter before exposing the cells. On the day of the test, after changing the medium in each well, samples were added and the plates incubated for 3 hours at 37° C. in the presence of 5% CO$_2$. Thereafter, the medium in the plates was removed and the cells washed twice with PBS (100 μl/well). Cell lysis solution (50 μl/well) was then added and the plates incubated for 30 minutes. After complete dissolution of cells by pipetting, each lysate was distributed in 20-μl portions into wells of a new 96-well plate and, further, 100 μl/well of a substrate solution (0.1 mM 4-methylumbelliferyl β-galactoside solution obtained by diluting a stock substrate solution prepared by dissolving 4-methylumbelliferyl β-D-galactoside in dimethylformamide to a final concentration of 1% with a substrate diluent comprising 10 mM sodium phosphate, pH 7.0, 100 mM NaCl, 1 mM MgCl$_2$, 0.1% BSA, and 0.05% NaN$_3$) was added, and the plate was covered with aluminum foil for shielding against light and allowed to stand at room temperature for 30 minutes. Fluorescence values (RU) were measured at the excitation wavelength of 365 nm and measurement wavelength of 450 nm using a fluorescent microplate reader. The results are shown in Table 3. The values shown are the values after subtraction of the fluorescence value for the untreated control group. Although β-galactosidase can be assayed by calorimetric method as well, the fluorescence method is superior from the standpoint of background and quantitative accuracy and precision.

In Table 3, the "standard values" are according to the Environmental Agency Notice No. 25 (1994) and the Environmental Agency Notice No. 14 (1994). The "detected value for each substance in the environment" is according to Akio Yasuhara, Environmental pollution by hazardous wastes, Mizu Kankyo Gakkaishi: vol. 17, No. 5, 1994 and Akio Yasuhara: Characteristics of leachates from landfills of waste, Kankyo to Sokutei Gijutsu: vol. 21, No. 4, 1994, and Masato Yamada and Yoshiro Ono, Risk assessment of residual bioaccumulable toxic chemical substances, Second symposium on aquatic environments: 1999.

perature for 30 minutes. Then, fluorescence values (RU) were measured at the excitation wavelength of 365 nm and

TABLE 3

β-Galactosidase inducing activities of various hazardous chemical substances in the environment

| Substance name | Sample concentration | Fluorescence value* | Detected value for each substance in the environment | Standard value |
|---|---|---|---|---|
| <Organic chemical substances> | | | | |
| Benzophenone | $0.5 \times 10^{-7}$~0.5 | 7.5~44 | N.D~$0.3 \times 10^{-3}$ | |
| Nonylphenol A | $10 \times 10^{-7}$~10 | 0~10 | | |
| Di(ethylhexyl)phthalate | $10 \times 10^{-7}$~10 | 0~13 | N.D~$6.4 \times 10^{-3}$ | |
| o-Dichlorobenzene | $1.3 \times 10^{-7}$~1.3 | 0~24 | $1 \times 10^{-3}$~0.13 | |
| Tetrachloroethylene | $0.6 \times 10^{-7}$~0.6 | 0~7.4 | $12 \times 10^{-3}$~0.6 | 0.1 |
| 1,1,2-Trichloroethane | $0.7 \times 10^{-7}$~0.7 | 0~10 | | 0.06 |
| 1,4-Dioxane | $2.2 \times 10^{-7}$~2.2 | 0~27 | N.D~0.3 | |
| Trichloroethylene | $0.7 \times 10^{-7}$~0.7 | 15~40 | $1 \times 10^{-3}$~0.32 | 0.3 |
| 1,2-Dichloroethane | $1.2 \times 10^{-7}$~1.2 | 1.0~6.9 | | 0.05 |
| Fluorene | $0.6 \times 10^{-7}$~0.6 | 0~10 | 0~0.0012 | |
| Phenanthrene | $0.5 \times 10^{-7}$~0.5 | 4.2~19 | | |
| <Metals> | | | | |
| Cadmium | $7.0 \times 10^{-2}$~8.9 | 5.3~14 | N.D~0.19 | 0.08 |
| Nickel | $13 \times 10^{-2}$~17 | 1.3~18 | N.D~5.1 | 0.17 |
| Lead | $4.0 \times 10^{-2}$~4.7 | 0~9.0 | N.D~1.9 | 0.04 |
| Antimony | $6.0 \times 10^{-2}$~8.0 | 0~11 | N.D~0.16 | 0.16 |

*: Fluorescence values (RU) in CHO 2F1813 cells.
Unit: μM

Using 5K95 cells, β-galactosidase activity measurements were carried out in the same manner. The results of comparison between 2F1813 and 5K95 are shown in FIGS. 3 to 6. Each value shown is the value after subtraction of the value for the untreated control group. [• 2F1813 and O5K95

In the figures, indicates each environmental standard concentration.

EXAMPLE 4

Reporter Protein Activity Values Measured Upon Addition of Microcystin

2F1813 and 5K95 cells were used. The medium used was MD medium (MCDB 302: 5.5 g/liter, D-MEM: 4.75 g/liter, L-glutamine: 0.3 g/liter, NaHCO$_3$: 1.27 g/liter, kanamycin: 0.1 g/liter, pH 7.1) supplemented with a final concentration of 5% of FBS and 200 μg/ml of G418, and culture was carried out at 37° C. in the presence of 5% CO$_2$. Two days before the test, the wells of a 96-well plate were seeded with $1\times10^4$ cells/100 μl/well. On the day of the test, after exchanging the medium in each well, microcystin dissolved in ethanol was distributed into wells in 10-μl portions of sample solution/well, followed by 3 hours of incubation at 37° C. in the presence of 5% CO$_2$. Thereafter, the medium was removed and, after washing with two portions of PBS, 50 μl/well of a cell lysis solution was added, and the plate was allowed to stand for 30 minutes. After complete dissolution of cells by pipetting, each lyzate was distributed in 20-μl portions into wells of a new 96-well plate and, further, 100 μl/well of a substrate solution (0.1 mM 4-methylumbelliferyl β-D-galactoside solution obtained by diluting a stock substrate solution prepared by dissolving 4-methylumbelliferyl β-D-galactoside in dimethylformamide to a final concentration of 1% with a substrate diluent comprising 10 mM sodium phosphate, pH 7.0, 100 mM NaCl, 1 mM MgCl$_2$, 0.1% BSA, and 0.05% NaN$_3$) was added, and the plate was covered with aluminum foil for shielding against light and allowed to stand at room temmeasurement wavelength of 450 nm using a fluorescent microplate reader. The results are shown in FIG. 7. The values shown are the values after subtraction of the fluorescence value for the untreated control group. Although β-galactosidase can be assayed by colorimetric method as well, the fluorescence method is superior from the background and quantitativeness viewpoint.

As a result, increases in β-galactosidase inducing activity were found within the microcystin concentration range of 10-4 to 25 μM.

EXAMPLE 5

Evaluation of Effects on Treatment of Landfill Leachate

There are 3 kinds of 1-liter reactors, namely, activated sludge (AS), activated carbon (AC) and biological activated carbon (BAC). The reactor conditions were as follows: temperature, 20° C.; HRT, 6 hr; and pH 7.0. Pellets for BAC treatment was prepared as activated carbon (100 g, wet weight) and activated sludge (MLSS of 2000 mg/L) for a few days. Thereafter, landfill leachate was allowed to flow thru the apparatus and the operation was started. To evaluate treatment, treatment water was analyzed for E-screen assay, reporter assay while bisphenol A and benzophenone concentrations were determined using GC/MS.

The evaluation of treatment capacity of landfill leachate was carried out using reporter assay employing 2F1813 cells. Cells transformed with HSP promoter were used as a specimen and cells transformed with SV40 promoter were used as a control. The assay was carried out as follows: a 96-well plate was seeded with $1\times10^4$ cells/well. The filtered sample (0.22 μm filter) was then added to each well and the cells were exposed for 3 hours. Thereafter, the substrate solution was added and the fluorescence intensities were measured at the excitation wavelength of 365 nm and the measurement wavelength of 450 nm.

E-screen assay was carried out according to the method of Soto et., al. (Environmental Health Perspectives, (103), 113, 1995). Human breast cancer cells (MCF-7) were cultured in DMEM medium (Sigma) at 37° C. in a 5% CO2 atmosphere. At the start of each experiment, both cell lines were seeded after passage into Falcon 24-well plates at 1×10$^4$ cells/well in 1 ml of the above medium. The cells were allowed to attach for 24 hr and then the medium was charged to phenol red-free DMEM containing charcoal striped serum. The sample was then added at 10 μl and the cells exposed for 6 days, after which, cell proliferation was assessed using the MTT assay.

Each treated sample was analyzed for the presence of bisphenol A and benzophenone as the trace amount of chemical contaminant analysis. The analysis was carried out by solid phase extraction method according to the provisional manual for exogenous endocrine disrupting chemical substances examination, Water Quality Bureau, Environmental Agency. GC/MS was carried out by using GC: HP5890 and MS: 5973 (both are being products of Agilent).

Results of GC/MS analysis and bioassay are shown in Tables 4 and 5.

TABLE 4

GC/MS analysis

| Treatment method | Bisphenol A (μg/l) | Benzophenone (μg/l) |
|---|---|---|
| Untreated water | 10,000 | 10,000 |
| Biological activated charcoal | 10.5 | 200 |
| Activated sludge | 9.2 | 1,800 |
| Activated charcoal | 3679 | 600 |

TABLE 5

Bioassay

| Treatment method | 2F1813 system (3 hr) | E-screen assay (250 hr) |
|---|---|---|
| Untreated water | 1.3 | 1.8 |
| Biological activated charcoal | 1.0 | 1.4 |
| Activated sludge | 1.3 | 1.7 |
| Activated charcoal | 1.2 | 1.6 |

Relative values are shown with the control value taken as 1.0.

The treatment evaluation using 2F1813 was correlated with trace amount of concentrations of environmental pollutants such a bisphenol A and benzophenone as determined by instrumental analysis, since the pre-treatment procedure was simplified and the evaluation time was curtailed dramatically, the effectiveness of this system was exhibited.

What is claimed is:

1. A cell
   which is obtained by transfer of a promoter containing a heat shock factor binding DNA sequence and a transcriptional regulatory sequence which functions in response to stress induction of a protein as a transcriptional regulatory factor binding site, as well as a reporter gene under the control of said promoter into a chromosome, said reporter gene being connected, on the downstream side thereof, to the SV40pA signal without any intervening intron, and
   which is usable for detecting chemicals or natural toxins which disrupt or disturb homeostasis in organisms, by measuring a protein inducing activity of said reporter gene,
   wherein the promoter containing the heat shock factor binding DNA sequence and the transcriptional regulatory sequence which functions on the occasion of stress induction of a protein as the transcriptional regulatory factor binding site, is an HSP47 promoter containing the heat shock factor binding DNA sequence and an SP1 factor binding sequence.

2. The cell according to claim 1, which is a transformant of a cultured animal cell.

3. The cell according to claim 1,
   which is a stable transformant of a Chinese hamster ovary cell or a HeLaS3 cell.

4. The cell according to claim 1,
   which is the Chinese hamster ovary cell-derived stable transformant 2F1813 (international deposition number FERM BP-7876).

5. A method for evaluating a test sample possibly containing a natural toxic substance and/or a hazardous chemical substance disrupting or disturbing homeostasis in living organisms,
   which comprises culturing the cell according to claim 1 in a medium containing said test sample, and
   then measuring a protein inducing activity of the reporter gene recited in claim 1.

6. The method according to claim 5,
   wherein said hazardous chemical substance is an endocrine disrupter.

7. The method according to claim 5,
   wherein said test sample is obtained from the environment, and said hazardous chemical substance is an environmental standard substance.

8. The method according to claim 5,
   wherein said hazardous chemical substance is a heavy metal.

9. The method according to claim 5,
   wherein said hazardous chemical substance is two or more different hazardous chemical substances in admixture, inclusive of an unidentified substance.

10. The method according to claim 5,
    wherein said natural toxic substance is a toxin produced by blue-green algae.

11. The method according to claim 5,
    wherein said natural toxic substance is microcystins or nodularins.

12. A kit for evaluating a test sample possibly containing a natural toxic substance and/or a hazardous chemical substance disrupting or disturbing homeostasis in living organisms,
    which comprises the cell according to claim 1.

* * * * *

UNITED STATES PATENT AND TRADEMARK OFFICE
CERTIFICATE OF CORRECTION

PATENT NO. : 6,740,521 B2
DATED : May 25, 2004
INVENTOR(S) : Hiroko Isoda et al.

It is certified that error appears in the above-identified patent and that said Letters Patent is hereby corrected as shown below:

<u>Title page,</u>
Item [73], should read as follows:
-- [73]  Assignees:  Kaneka Corporation, Osaka (JP);
**National Institute of Advanced
Industrial Science and Technology (AIST),
Administrative Institution (IAI)** under
Ministry of Economy, Trade and Industry,
Tokyo (JP) --

Signed and Sealed this

Twenty-third Day of November, 2004

JON W. DUDAS
*Director of the United States Patent and Trademark Office*